United States Patent [19]
Rothgery et al.

[11] Patent Number: 5,433,802
[45] Date of Patent: Jul. 18, 1995

[54] USE OF REDUCED VOLATILITY SUBSTITUTED HYDRAZINE COMPOUNDS IN LIQUID PROPELLANTS

[75] Inventors: Eugene F. Rothgery, North Branford; Karl O. Knollmueller, Hamden; Steven A. Manke, Wallingford; Frank W. Migliaro, Waterbury, all of Conn.

[73] Assignee: Olin Corporation, Cheshire, Conn.

[21] Appl. No.: 283,429

[22] Filed: Aug. 1, 1994

[51] Int. Cl.⁶ ............................................. C06B 47/08
[52] U.S. Cl. .................................... 149/36; 149/74; 149/109.6; 149/120
[58] Field of Search ................. 149/36, 74, 109.6, 120; 60/218, 219

[56] References Cited

PUBLICATIONS

Koltunov et al., Kinetics of Reactions of Neptunium and Plutonium ions with Hydrazine Derivatives, *Radiokhimiya* 33(5) pp. 99–107, 1991, (Chem Abstract).

*Primary Examiner*—Donald P. Walsh
*Assistant Examiner*—Anthony R. Chi
*Attorney, Agent, or Firm*—Dale L. Carlson

[57] ABSTRACT

The present invention relates to a liquid or gel propellant comprising an oxidizer and a fuel, said fuel preferably having a vapor pressure not exceeding 10 millimeters of mercury at 25° C. and being selected from the group consisting of hydroxy-(lower alkyl)-hydrazine, dihydroxy-(lower alkyl)hydrazine, cyanoethylhydrazine, 1-methyl-1-cyanoethylhydrazine, 1,1-dimethyl-2-cyanoethylhydrazine, and combinations thereof. Also claimed is a method of making the propellant.

14 Claims, No Drawings

USE OF REDUCED VOLATILITY SUBSTITUTED HYDRAZINE COMPOUNDS IN LIQUID PROPELLANTS

FIELD OF THE INVENTION

The present invention relates generally to a new class of propellants and, more specifically to substituted hydrazine propellants characterized primarily by reduced vapor pressures.

BACKGROUND OF THE INVENTION

Hydrazine, monomethylhydrazine and unsym-dimethylhydrazine have had a long and successful history of use as liquid propellants in rockets and in thrusters. These conventional hydrazine compounds are still extensively used, but have come under regulatory pressure due to toxicity concerns, due in large part to their relatively high vapor pressure at ambient temperatures (e.g., 20° C.–30° C.).

New, hydrazine-based compounds exhibiting lower vapor pressures compared to the above-mentioned conventional hydrazine compounds, while still providing excellent propellant properties, such as a high specific impulse, would be highly desired by the military and the commercial propellants community. The present invention provides several new hydrazine-based fuels having such advantageous propellant properties.

SUMMARY OF THE INVENTION

In one aspect, the present invention relates to a liquid or gel propellant comprising an oxider (preferably selected from the group consisting of fuming nitric acid, nitrogen tetroxide, mixed oxides of nitrogen {e.g., a mixture of 10%–25% of NO with 75%–90% by weight of $N_2O_4$}, and combinations thereof) and a fuel selected from the group consisting of hydroxy-(lower alkyl)-hydrazine (such as hydroxyethylhydrazine, hydroxypropylhydrazine, and hydroxybutylhydrazine), dihydroxy-(lower alkyl)hydrazine (such as di-(hydroxyethyl)-hydrazine, di-(hydroxypropyl)-hydrazine, and di-(hydroxy-butyl)hydrazine), cyanoethylhydrazine (also referred to herein as "CEH"), 1-methyl-1-cyanoethylhydrazine (also referred to herein as "MCEH"), 1,1-dimethyl-2-cyanoethylhydrazine (also referred to herein as "DMCEH"), and combinations thereof.

In another aspect, the present invention relates to a bipropellant composition comprising an oxidizer selected from the group consisting of fuming nitric acid, nitrogen tetroxide, mixed oxides of nitrogen, and combinations thereof, and a fuel selected from the group consisting of hydroxy-(lower alkyl)-hydrazine, dihydroxy-(lower alkyl)-hydrazine, CEH, MCEH, DMCEH, and combinations thereof.

In yet another aspect, the present invention relates to a method of making a propellant which comprises contacting an oxidizer selected from the group consisting of fuming nitric acid, nitrogen tetroxide, mixed oxides of nitrogen, and combinations thereof, and a fuel selected from the group consisting of hydroxy-(lower alkyl)-hydrazine, dihydroxy-(lower alkyl)-hydrazine, CEH, MCEH, DMCEH, and combinations thereof.

The fuel employed in the above-described method and compositions preferably has a vapor pressure not exceeding 10 millimeters of mercury at 25° C.

These and other aspects will become apparent upon reading the following detailed description of the invention.

DETAILED DESCRIPTION OF THE INVENTION

The present inventors have surprisingly found that a select group of substituted hydrazine compounds provides an excellent combination of low vapor pressure at room temperature, and excellent specific impulse during use as a liquid propellant in mono- or bi-propellant applications. This finding is particularly surprising in view of the relatively high vapor pressure of conventionally-employed hydrazine propellants, including hydrazine, monomethylhydrazine and unsymmetrical dimethylhydrazine (abbreviated herein as "unsym-dimethylhydrazine").

Several of the substituted hydrazine compounds useful in the present invention have been disclosed in the technical literature as being useful as intermediates in the synthesis of various heterocyclic molecules. For example, the reaction of hydrazine with an oxirane to produce the corresponding hydroxyalkylhydrazine, such as the reaction of hydrazine with ethylene oxide to give hydroxyethylhydrazine, is known. Hydroxyethylhydrazine has been used as a chemical intermediate and for use as an agricultural chemical. However, the use of these compounds in propellant applications was not known heretofore, based upon the knowledge of the present inventors.

In accordance with the present invention, these substituted hydrazine compounds, produced by reacting a conventional hydrazine compound, such as hydrazine, monomethylhydrazine, unsym-dimethylhydrazine, or a combination thereof, with a co-reactant selected from the group consisting of acrylonitrile, $C_1$ to $C_6$ alkylene oxides (such as ethylene oxide, propylene oxide, and butylene oxide) and combinations thereof, has been found by the present inventors to provide a hydrazine-containing propellant product having excellent propellant properties.

The hydrazine-based propellant product of the present invention is typically a high-boiling, reduced vapor pressure, clear liquid providing excellent performance efficacy during use as a liquid or gel fuel for rockets or as a liquid or gel gun propellant. As a group, these fuels provide many of the favorable performance characteristics of the hydrazine starting reactants, including favorable heats of formation and hypergolicity (spontaneous ignition on contact with the oxidizer, thereby avoiding the need for a separate ignition source), while having a greatly reduced vapor pressure and volatility at room temperature. This decreased volatility reduces the likelihood of vapor toxicity concerns, as compared to those associated with current hydrazine fuels.

The propellants of the present invention are suitably employed as a liquid fuel together with an oxidant in bipropellant compositions. Preferably, the bipropellant composition comprises an oxidizer selected from the group consisting of fuming nitric acid, nitrogen tetroxide, mixed oxides of nitrogen, and a liquid fuel (preferably having a vapor pressure not exceeding 10 millimeters of mercury at 25° C.) selected from the group consisting of hydroxy-(lower alkyl)-hydrazine, dihydroxy-(lower alkyl)hydrazine, CEH, MCEH, DMCEH, and combinations thereof.

As an alternative to the use of single component propellants, there may be advantages in blending various compounds in order to custom tailor a desired set of properties such as melting points, viscosities or the like. Furthermore, gelling agents are suitably employed for gelling the liquid propellants in certain applications, if desired. Illustrative gelling agents, which have previously been disclosed for use with hydrazine and methylhydrazine in propellant applications, include cellulose and hydroxyalkylcellulose, such as hydroxypropylcellulose and hydroxyethylcellulose, gelling agents. These gelling agents are suitably employed in the compositions of the present invention. Additional discussion of gelling agents and their use to provide gelled hydrazine-based fuels containing finely divided metallic fuel particles (e.g. aluminum, magnesium, boron, beryllium, lead, and zirconium, and hydrides thereof) is found in U.S. Pat. Nos. 3,857,743 and 4,039,360, the disclosures of which are incorporated herein by reference in their entirety.

The following examples are intended to illustrate, but in no way limit the scope of, the present invention. As used herein, the term "lower alkyl" is intended to designate an alkyl moiety having between one and six carbon atoms.

EXAMPLE 1

Preparation of 1,1-dimethyl-2-cyanoethylhydrazine (DMCEH) Propellant

Unsym-dimethylhydrazine (UDMH), (38 ml, 0.5 mole) was mixed with 40 ml of water, warmed to 87° C. and the addition of acrylonitrile (39 ml, 0.5 mole) begun. The reaction was carried out during the course of 2 hours with the temperature reaching that or reflux. The mixture was refluxed an additional two hours, and then cooled to 40° C. when a vacuum was placed on the apparatus. When the vacuum reached 4 torr, heating was begun. The first cut from the mixture was removed and discarded, and a second fraction taken, having a boiling point of 77°–81° C. at a pressure of 4 torr. The product was characterized by NMR, IR and elemental analyses. A heat of combustion was determined in order to calculate the heat of formation for the product.

EXAMPLE 2

Preparation of cyanoethylhydrazine (CEH) Propellant

64% Hydrazine solution (28 ml, 0.58 mole) was placed in a flask and acrylonitrile (39 ml, 0.5 mole) slowly added while cooling the mixture. The addition was carried out over a period of two hours with a maximum temperature of 21° C. The resulting mixture was vacuum distilled at 3.5 torr. The first cut of water and hydrazine was discarded and a middle cut boiling at 105° C./1.9 torr was collected. It was characterized by NMR, IR and elemental analyses. A heat of combustion was determined in order to calculate the heat of formation for the product.

EXAMPLE 3

Preparation of 1-methyl-1-cyanoethylhydrazine (MCEH) Propellant

Monomethylhydrazine (MMH) (46 g, 1 mole) was placed in a flask and acrylonitrile (53.1 g, 1 mole) was slowly added dropwise, maintaining the temperature at 40° C. with a cold water bath. The mixture was post-reacted at 70° C. for 30 minutes. The product was vacuum distilled at 69° C./0.95 torr. A middle cut was isolated as a clear, white liquid.

EXAMPLE 4

Calculated Performances for the Propellants of Ex 1-3

The performance of each of the candidate propellants prepared in Examples 1 through 3, as well as mixtures thereof, was calculated employing computer software written for this purpose. The software used was "Newpep" which was developed by the Naval Air Weapons Center, China Lake, Calif. The fuels and mixtures evaluated were stoichiometric with the oxidizer nitrogen tetroxide. Calculations for two currently used fuels, hydrazine and methylhydrazine are included for comparison. As can be seen the performances of the claimed substances compare very well. Since the new materials have greater densities than MMH, the performances are actually better on a density-$I_{sp}$ basis.

| FUEL | SPECIFIC IMPULSE, SEC |
|---|---|
| CEH | 276.9 |
| MCEH | 280.8 |
| DMCEH | 270.4 |
| HEH | 273.4 |
| 5% HEH 95% MCEH | 276.9 |
| 10% HEH 90% MCEH | 276.7 |
| 15% HEH 85% MCEH | 276.6 |
| Hydrazine | 277 |
| Methylhydrazine | 287.2 |

As an alternative to the use of single component propellants, there may be advantages in blending various compounds in order to custom tailor a desired set of properties such as melting points, viscosities or the like.

EXAMPLE 6

Summary of Properties

| PROPERTY | CEH | MCEH | DMCEH | HEH |
|---|---|---|---|---|
| CAS No. | 353-07-1 | 352-90-9 | 22705-94-8 | 109-8-42 |
| Formula | $C_3H_7N_3$ | $C_4H_9N_3$ | $C_5H_{11}N_3$ | $C_2H_8N_2O$ |
| Molecular Wt. | 85.11 | 99.13 | 113.16 | 76.10 |
| Boiling Point, °C. @ mm/Hg | 85 @ 0.35 | 95 @ 10 | 80 @ 4 | 140 @ 9 |
| V.P. mm Hg @ 25° C. | <1 | 4 | <1 | <1 |
| Heat of Formation, Kcal/m | +18.4 | +30.2 | +39.5 | −46.4 |
| Density, g/cm$^3$ | 1.055 | 0.974 | | 1.113 |
| Hypergolic with RFNA | yes | yes | yes | yes |

EXAMPLE 7

Comparison of Boiling Points and Vapor Pressures

One of the primary advantages of the use of the propellant compounds of the present invention is their low vapor pressures as compared to conventional propellant hydrazines. The currently used hydrazines perform well, but vapor-phase toxicity concerns have been raised. The compounds of the present invention provide a excellent combination of the excellent attributes of hydrazine such as favorable heat of formation, liquid state, and hypergolicity, while possessing higher boiling points and reduced vapor pressures, as compared to the above-mentioned conventional propellant hydrazines.

| Compound | Boiling Pt., °C | Vapor Pressure at 25° C., torr |
|---|---|---|
| Hydrazine | 114 @ 760 torr | 142 |
| Methylhydrazine | 88 @ 760 torr | 49.5 |
| u-Dimethylhydrazine | 62 @ 760 torr | 167 |
| Cyanoethylhydrazine | 85 @ 4 torr | ≦1 |
| Methylcyanoethylhydrazine | 95 @ 10 torr | 4 |
| Hydroxyethydrazine | 140 @ 9 torr | 0.01 |

Although the mono-reaction product of acrylonitrile with the three currently used propellant hydrazines has been prepared in the above examples, as well as hydroxyethylhydrazine reaction product, the invention is not intended to be limited by these examples. For example, as another alternative, the reaction conditions or molar ratio of reactants is suitably varied as desired, i.e. varying reactant ratios, reaction temperatures or orders of addition of the reactants. In this fashion, the following derivative propellant compounds are suitably prepared in accordance with the present invention:

1. Di(cyanoethyl)hydrazine (two possible isomers)
2. Tri(cyanoethyl)hydrazine
3. Tetra(cyanoethyl)hydrazine
4. Di(cyanoethyl)-methylhydrazine (two possible isomers)
5. Tri(cyanoethyl)-methylhydrazine
6. Di(cyanoethyl)-dimethylhydrazine
7. Di(2-hydroxyethyl)hydrazine
8. 2-Hydroxyethyl-methylhydrazine
9. 2-Hydroxyethyl-dimethylhydrazine While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A liquid or gel propellant comprising an oxidizer and a fuel, said fuel being a dihydroxy-(lower alkyl)-hydrazine selected from the group consisting of di-(hydroxyethyl)hydrazine, di-(hydroxypropyl)-hydrazine, di-(hydroxybutyl)-hydrazine), and combinations thereof, said propellant containing a molar ratio of said oxidizer to said fuel of between about 10 to 1 and about 1 to 10.

2. The propellant of claim 1 wherein said oxidizer is selected from the group consisting of fuming nitric acid, nitrogen tetroxide, mixed oxides of nitrogen, and combinations thereof.

3. The propellant of claim 1 wherein said fuel has a vapor pressure not exceeding 10 millimeters of mercury at 25° C.

4. A bipropellant composition comprising an oxidizer selected from the group consisting of fuming nitric acid, nitrogen tetroxide, mixed oxides of nitrogen, and combinations thereof, and a fuel selected from the group consisting of hydroxy-(lower alkyl)-hydrazine, dihydroxy-(lower alkyl)-hydrazine, cyanoethylhydrazine, 1-methyl-1-cyanoethylhydrazine, 1,1-dimethyl-2-cyanoethylhydrazine, and combinations thereof.

5. The bipropellant of claim 4 wherein said hydroxy-(lower alkyl)-hydrazine is selected from the group consisting of hydroxyethylhydrazine, hydroxypropylhydrazine, hydroxybutylhydrazine, and combinations thereof.

6. The bipropellant of claim 4 wherein said dihydroxy-(lower alkyl)-hydrazine is selected from the group consisting of di-(hydroxyethyl)-hydrazine, di-(hydroxypropyl)-hydrazine, di-(hydroxy-butyl)hydrazine), and combinations thereof.

7. The bipropellant of claim 4 wherein the molar ratio of said oxidizer to said fuel is between about 10 to 1 and about 1 to 10.

8. The bipropellant of claim 4 wherein said fuel has a vapor pressure not exceeding 10 millimeters of mercury at 25° C.

9. A method of making a propellant which comprises contacting an oxidizer selected from the group consisting of fuming nitric acid, nitrogen tetroxide, mixed oxides of nitrogen, and combinations thereof, and a fuel selected from the group consisting of hydroxy-(lower alkyl)-hydrazine, dihydroxy-(lower alkyl)-hydrazine, cyanoethylhydrazine, 1-methyl-1-cyanoethylhydrazine, 1,1-dimethyl-2-cyanoethylhydrazine, and combinations thereof.

10. The method of claim 9 wherein said hydroxy-(lower alkyl)-hydrazine is selected from the group consisting of hydroxyethylhydrazine, hydroxypropylhydrazine, hydroxybutylhydrazine, and combinations thereof.

11. The method of claim 9 wherein said dihydroxy-(lower alkyl)-hydrazine is selected from the group consisting of di-(hydroxyethyl)-hydrazine, di-(hydroxypropyl)-hydrazine, di-(hydroxy-butyl)hydrazine), and combinations thereof.

12. The method of claim 9 wherein the molar ratio of said oxidizer to said fuel is between about 10 to 1 and about 1 to 10.

13. The method of claim 9 wherein said mixed oxides of nitrogen comprises a mixture of between about 10% and about 25% of NO, and between 75% and about 90% of N204, based upon the total weight of said mixed oxides.

14. The method of claim 9 wherein said fuel has a vapor pressure not exceeding 10 millimeters of mercury at 25° C.

* * * * *